United States Patent [19]

Herrin

[11] Patent Number: 4,778,385

[45] Date of Patent: Oct. 18, 1988

[54] METHOD AND APPARATUS FOR COMPOSITE RESTORATION USING A COMPOSITE MATRIX

[75] Inventor: Hermon K. Herrin, Houston, Tex.

[73] Assignee: Board of Regents, The University of Texas System, Austin, Tex.

[21] Appl. No.: 65,313

[22] Filed: Jun. 22, 1987

[51] Int. Cl.⁴ .............................................. A61C 9/00
[52] U.S. Cl. .................................................... 433/40
[58] Field of Search .................... 433/40, 39, 149, 228

[56] References Cited

U.S. PATENT DOCUMENTS

| | | | |
|---|---|---|---|
| 4,303,389 | 12/1981 | Salsarulo | 433/60 |
| 4,631,030 | 12/1986 | Weissenflu | 433/229 |
| 4,696,646 | 12/1987 | Maitland . | |

*Primary Examiner*—Robert Peshock
*Attorney, Agent, or Firm*—Arnold, White & Durkee

[57] ABSTRACT

The invention disclosed herein relates to a composite matrix for use in the composite restoration of a posterior tooth whose proximal surface has been partially removed due to decay. The composite matrix of the present invention is intended for permanent installation on the tooth during the restoration process.

15 Claims, 3 Drawing Sheets

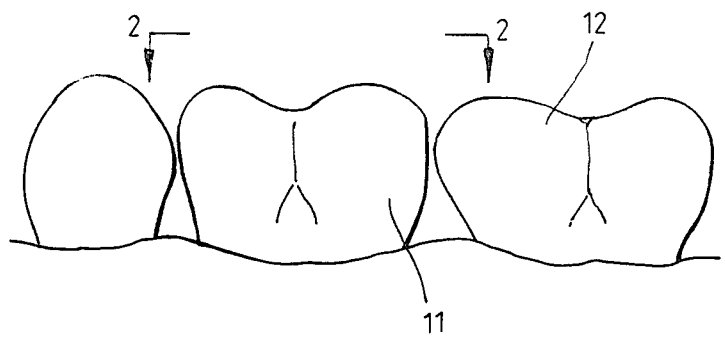
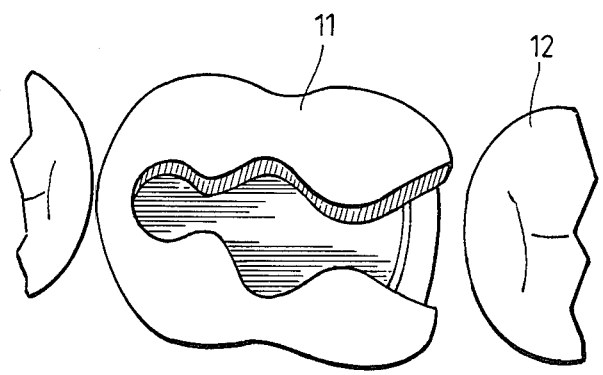
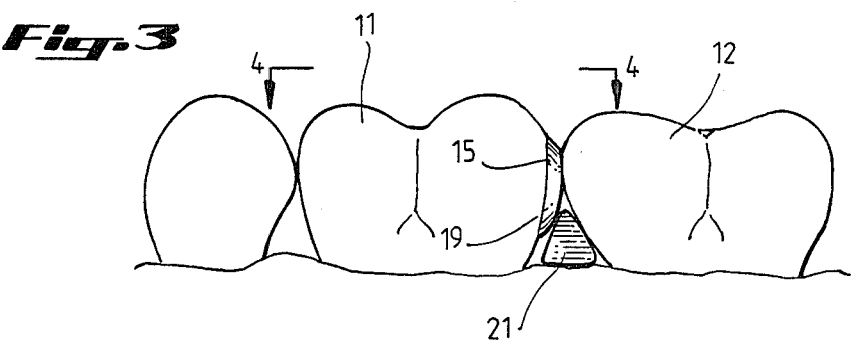
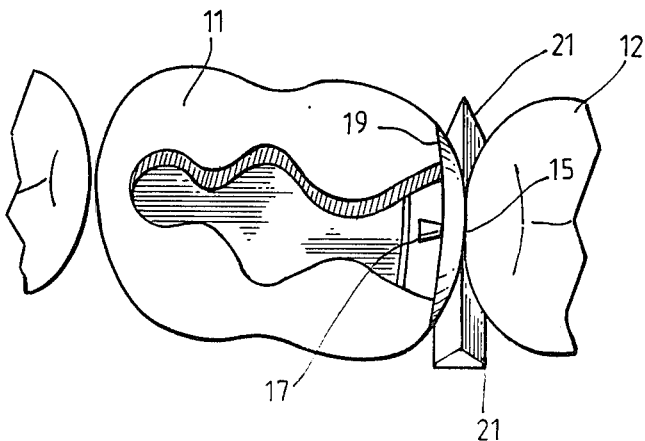

METHOD AND APPARATUS FOR COMPOSITE RESTORATION USING A COMPOSITE MATRIX

BACKGROUND OF THE INVENTION

1. Field of the Invention

The invention disclosed herein relates to a composite matrix for use in the composite restoration of a posterior tooth whose proximal surface has been partially removed. The composite matrix of the present invention is intended for permanent installation on the tooth during the restoration process.

2. Description of the Prior Art

The removal of decayed material from teeth leaves a void or cavity which is typically filled in normal dentistry procedure. The filling of the void or cavity is known as restoration. For many years, metal alloys, known as dental amalgam alloys, were used as fillings or restoration material.

In recent years, composite materials have gained increasing acceptance as an alternative to dental amalgam alloys for the restoration of posterior teeth. Composite restoration material closely resembles the tooth in color, and thus provides a more aesthetically pleasing appearance in the tooth than does a dental amalgam alloy.

In the prior art, a matrix band is wrapped around the tooth after the decayed material is removed in order to define a volume which will contain the composite restoration material. After the composite restoration material is placed in the void and cured, the matrix band is removed. The use of a temporarily installed matrix band involves several problems.

First, the removal of the matrix band often results in leaving an exposed gap between the composite restoration material and the tooth's surface. Second, the exposed composite restoration material on the outer proximal surface of the tooth is subject to proximal abrasion. Third, microleakage may occur through the exposed composite restoration material on the proximal surface of the tooth.

SUMMARY OF THE INVENTION

The present invention employs a matrix made from the same material as the composite restoration material. This matrix is intended to be permanently installed on the tooth, thus dealing with the problems of the prior art, discussed above.

In a preferred embodiment, the composite matrix has an inner surface configured to conform to the geometry of the posterior tooth's proximal surface. In most instances the inner surface will be generally concave. This concave geometry allows for a tight bonding between the tooth and the composite matrix. The outer surface of the composite material is generally convex, thus resembling the geometry of the posterior tooth surface which it replaces.

The matrix should be sufficiently wide and high to cover the opening in the proximal surface leading to the cavity to be filled. Typically, the matrix will resemble a small plate, membrane, or form about 5 millimeters wide, 4 millimeters high and less than 0.2 millimeters thick. It may be ground or otherwise trimmed to fit the opening it is to cover.

As mentioned above, the matrix is preferably made of the same composite material which is used in filling the cavity. A number of such materials are well known, and generally comprise a mixture of a cross linking polymer and a filler. A typical polymer which finds wide-spread current use is bis-GMA. This particular polymer is most often used with a light-cured bonding agent.

The edges of the matrix may be beveled or otherwise fitted to the edge of the opening to which it is applied. The inner, concave surface of the matrix may be ribbed or otherwise configured to effect an intimate and permanent bond with the restoration material in the cavity. A preferred interlocking device is a flared peg or similar anchoring member extending from the inner surface of the matrix into the cavity. The peg or other anchoring member is preferably an integral part of the composite matrix and therefore of the same composition as the matrix and the restoration material.

A method embodiment of the present invention involves applying a bonding agent to the proximal surface of the tooth and the inner surface of the composite matrix, placing the inner surface of the composite matrix firmly against the proximal surface of the tooth, filling the void in the tooth with composite restoration material that is identical in composition to the material from which the composite matrix is made, and curing the bonding agent.

In a preferred embodiment of the method invention, wedges are used in placing the composite matrix firmly against the proximal surface of the tooth to ensure a tight fit. After the bonding agent has been cured, the wedges are removed.

In another preferred embodiment, any excess composite matrix material is removed and bonding agent is applied to any spaces appearing between the composite matrix and the tooth, and the composite restoration material and the composite matrix. These spaces are known as margins.

DESCRIPTION OF THE DRAWINGS

FIG. 1 is a side view of a posterior tooth with decayed material removed from its proximal surface.

FIG. 2 is a top view of the tooth shown in FIG. 1, taken along line 2—2.

FIG. 3 is a side view of the tooth shown in FIG. 1 with a composite matrix held in place by a wedge.

FIG. 4 is a top view of the tooth shown in FIG. 3, taken along line 4—4.

DESCRIPTION OF THE PREFERRED EMBODIMENTS

In FIG. 1, a posterior tooth 11 is shown in a gum between two other teeth as it would typically appear in a mouth. The right proximal side of the tooth 11 has a flat vertical surface where decayed material has been removed.

Referring to FIG. 2, decayed material has been removed from the occlusal surface and the right proximal wall of tooth 11.

The composite matrix 15 is affixed to the right proximal wall of tooth 11, as shown in FIG. 3. Bonding agent 19 is applied to the inner surface of composite matrix 15 and tooth 11. Wedge 21 is inserted in the interproximal space between teeth 11 and 12 to hold composite matrix 15 firmly in place during the time period that bonding agent 19 cures.

Figure 5:
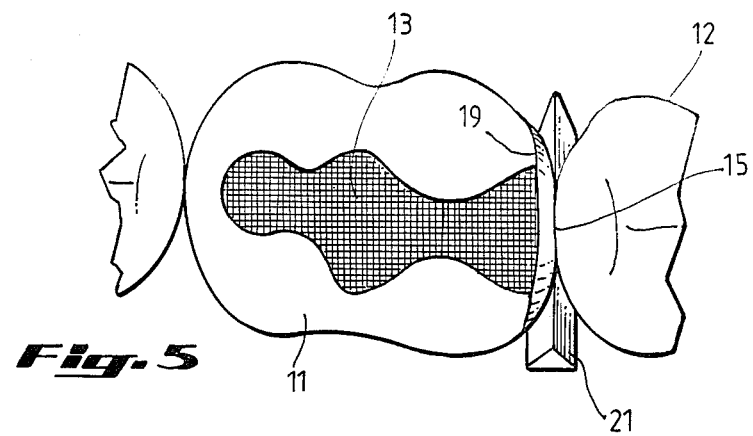
FIG. 5 is a top view of the tooth shown in FIG. 4 with composite restoration material filling the volume left by the removal of decayed tooth material.

FIG. 4 is a top view of tooth 11, composite matrix 15 and wedge 21 assembled in the arrangement shown in FIG. 3. Flared member 17 (see also FIG. 8) extends inward from the inner surface of composite matrix 15 to serve as an anchoring member when composite restoration material 13 is poured into tooth 11, as shown in FIG. 5.

Figure 6:
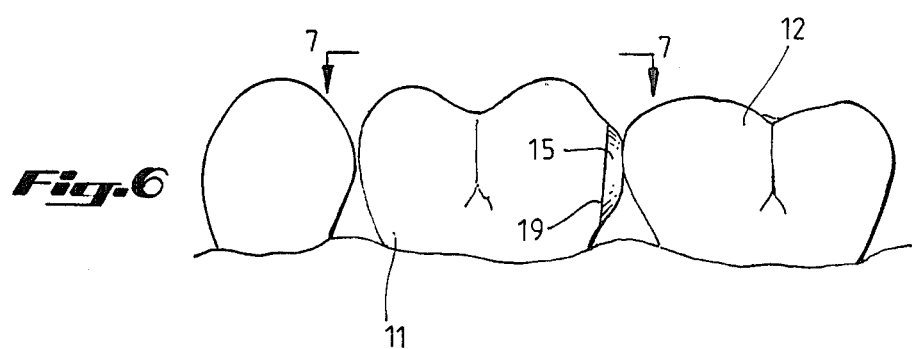
FIG. 6 is a side view of the tooth shown in FIG. 3 with a composite matrix firmly adhered to the side of the tooth.
Figure 7:
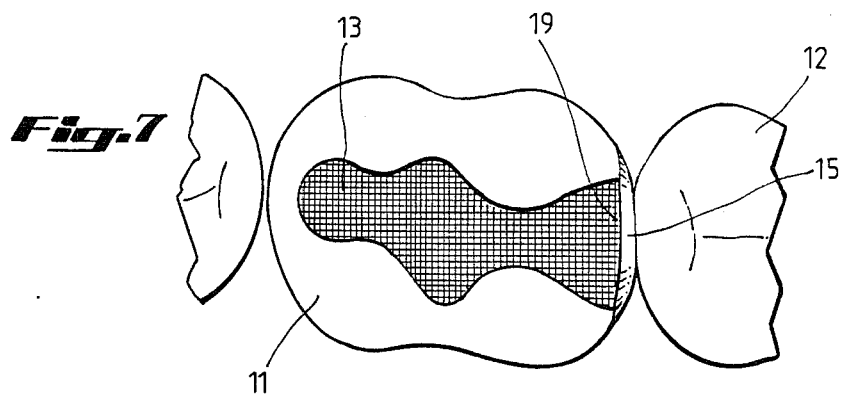
FIG. 7 is a top view of the tooth shown in FIG. 6, taken along line 7—7.

After bonding agent 19 has cured, wedge 21 is removed leaving composite matrix 15 bonded onto the side of tooth 11 as shown in FIGS. 6 and 7.

Figure 8:
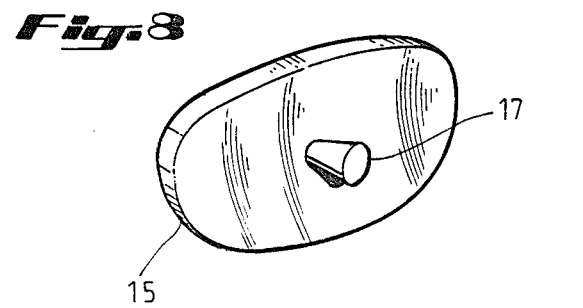
FIG. 8 is an isometric view of a preferred embodiment of the composite matrix.

In a preferred embodiment, composite matrix 15 is an oval shaped membrane having a thickness of less than 0.2 millimeters with a flared member 17 extending inward from the concave inner surface, as shown in FIG. 8.

Figure 9:
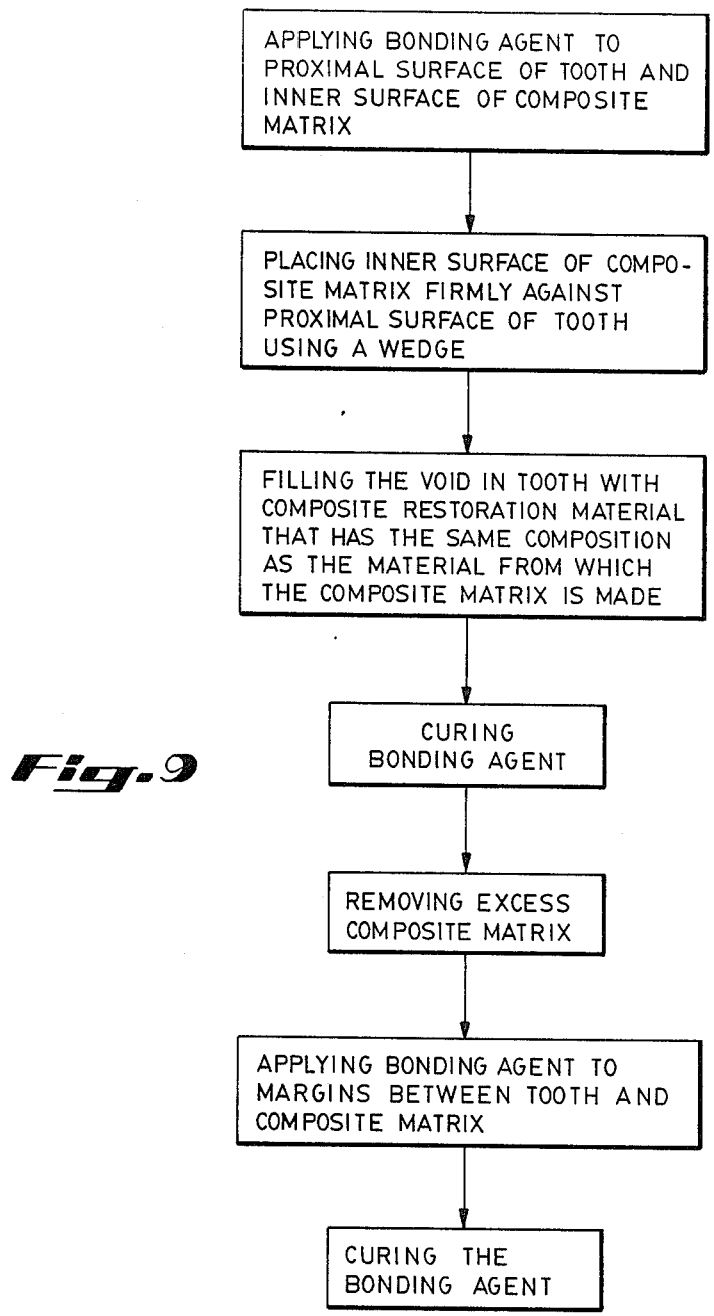
FIG. 9 is a block diagram of the steps in the present method invention.

A method embodiment of the present invention is set out in FIG. 9. Bonding agent 19, typically in the form of a cream or paste, is applied to the proximal surface of the tooth 11 and the inner surface of composite matrix 15. The inner surface of composite matrix 15 is placed firmly against the proximal surface of tooth 11. A wedge 21 is used to secure composite matrix 15 firmly against the proximal surface of tooth 11.

The void in tooth 11 is filled with composite restoration material 13 that is identical in composition to the material from which composite matrix 15 is made. The bonding agent 19 is then cured. An acceptable curing method is exposing bonding agent 19 to a light source. After the curing process is completed, wedge 21 is removed.

In another preferred embodiment of the method invention, any excess composite matrix 15 remaining after the curing process is removed. In some instances, composite restoration material 13 undergoes some shrinkage, resulting in exposed margins between tooth 11 and composite matrix 15, and the composite restoration material 13 and the composite matrix 15. In these cases, bonding agent 19 is applied to the exposed margins and cured.

Many modifications and variations may be made in the embodiments described herein and depicted in the accompanying drawings without departing from the concept of the present invention. Accordingly, it is clearly understood that the embodiments described and illustrated herein are illustrative only and are not intended as limitations upon the scope of the present invention.

What is claimed is:

1. A matrix for use in the composite restoration of a posterior tooth proximal surface, said matrix having a concave inner surface for adhesion to the tooth, and said matrix being made of the same material as the composite restoration.

2. The matrix of claim 1, further comprising a flared member extending inward from the concave surface.

3. The matrix of claim 1, wherein said composite matrix is an oval shaped membrane.

4. The matrix of claim 1, wherein the outer surface of said composite matrix is convex.

5. A matrix for use in the composite restoration of a posterior tooth proximal surface said matrix being made of the same material as the composite restoration and having a thickness of less than about 0.2 millimeters.

6. The matrix of claim 5, wherein the inner surface of said matrix is concave and the outer surface of said matrix is convex.

7. The matrix of claim 6, further comprising a flared member extending inward from the concave surface.

8. A posterior tooth including a restored cavity which extends through the proximal surface of the tooth, comprising:
   (a) composite restoration material filling the cavity in said tooth;
   (b) a composite matrix made of the same material as said composite restoration material and bonded to said composite restoration material and to the proximal surface of said tooth; and
   (c) bonding agent on the mating surfaces of said tooth and said composite matrix.

9. A method of composite restoration of a posterior tooth having a void which includes a portion of its proximal surface, comprising the steps of:
   (a) applying bonding agent to the proximal surface of the tooth and the inner surface of a composite matrix adapted to fit against the proximal surface and cover the void in the proximal surface;
   (b) placing the inner surface of the composite matrix firmly against the proximal surface of the tooth so as to cover the void in the proximal surface;
   (c) filling the void in the tooth with composite restoration material that has the same composition the material from which the composition matrix is made; and
   (d) curing the bonding agent.

10. The method of claim 9, which further comprises the step of wedging the composite matrix firmly against the proximal surface of the tooth.

11. The method of claim 10, further comprising the step of removing the wedge after curing the bonding agent.

12. The method of claim 11, further comprising the steps of:
   (a) removing excess composite matrix from the restored tooth;
   (b) applying bonding agent to margins between the tooth and the composite matrix;
   (c) applying bonding agent to margins between the composite restoration material and the composite matrix; and
   (d) curing the bonding agent 13. A matrix for use in the composite filling of a posterior tooth wherein the restoration includes the filling of a cavity and a contiguous opening in a proximal surface of the tooth, which comprises a plate-like member configured to cover the opening and fit against the proximal surface, said member having substantially the same composition as the composite filling.

14. The matrix of claim 13 in which the member has a generally convex outer surface.

15. The matrix of claim 14 in which the member has a generally concave inner surface.

* * * * *